United States Patent [19]

Pascuchi

[11] Patent Number: 4,978,687
[45] Date of Patent: Dec. 18, 1990

[54] ANTI-VIRAL AGENT

[75] Inventor: Josep M. V. I. Pascuchi, Barcelona, Spain

[73] Assignee: Rhoderton Corporation N.V., Curacao, Netherlands

[21] Appl. No.: 394,240

[22] Filed: Aug. 14, 1989

Related U.S. Application Data

[63] Continuation of Ser. No. 140,352, Jan. 4, 1988, abandoned.

[30] Foreign Application Priority Data

Dec. 8, 1987 [GB] United Kingdom ............... 8728625

[51] Int. Cl.$^5$ ............................................. A61K 31/10
[52] U.S. Cl. ..................................... 514/708; 514/711
[58] Field of Search ............................. 514/708, 711

[56] References Cited

U.S. PATENT DOCUMENTS 3,334,012  8/1967  Herschler ........................... 514/708
4,616,039 10/1986  Herschler ........................... 514/711

OTHER PUBLICATIONS

McGready, Sr.; The Persecuted Drug—The Story of DMSO, (1981), 125–127, 268, 285 and 286.
Rammler et al., (3/67), Annals New York Academy of Sciences, 141:13–23.
Warren S. MacGregor, (3/67), Annals New York Academy of Sciences, 141:3–12.
Harold Varmus, (6/88), Science, 240:1427–1435.
Mitsuya et al., (2/87), Nature, 325:773–778.
Klatzmann et al., (1/86), Nature, 319:10–11.
Author Unknown, (7/88), New Scientist, p. 33.
Bernard C. Smale, (Autumn 1969), The Sulphur Institute Journal, pp. 2–6.
Chan et al., (10/68), Applied Microbiology, 16:1625–1626.
Wallis et al., (9/68), Journal of Virology, 2:953–954.
Jacob et al., (9/67), Am. Journal of Surgery, 114:414–426.
Willhite et al., (1984), Journal of Applied Toxicology, 4:155–160.
Jimenez et al., (1982), J. Lab. Clin. Med., 100:489–500.
Ramirez et al., (Mar. 15, 1967), Annals New York Academy of Sciences, 141:655–677.
Trice et al., (1985), Seminars in Arthritis and Rheumatism, 15:45–60.
Broder et al., (1985), Ann. Rev. Immunol. 3:321–336.
Hirsch et al., (1985), Annals of Internal Medicine, 103:750–755.
Dolin, (1985), Science, 227:1296–1303.
Wong-Staal et al., (1985), Nature, 317:395–403.

Primary Examiner—Jerome D. Goldberg
Attorney, Agent, or Firm—Irell & Manella

[57] ABSTRACT

A method of treating an infection attributable to a retrovirus comprises the step of administering to the patient at effective amount of a compound of formula (I):

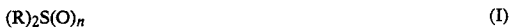

wherein R is methyl or ethyl and n is 1 or 2.

10 Claims, No Drawings

ANTI-VIRAL AGENT

This application is a continuation of application Ser. No. 140,352, filed Jan. 4, 1988, now abandoned.

FIELD OF THE INVENTION

The present invention relates to the treatment of human or animal infections attributable to a retrovirus.

BACKGROUND TO THE INVENTION

Dimethylsulphoxide (DMSO) is a known compound, a colourless oily liquid, for which a variety of physiologic properties have been described. For example, it has local analgesic and anti-inflammatory effects, is bacteriostatic, acts as a diuretic inducing a negative salt balance, has a tranquilising effect and potentiates the effects of other compounds. It is also an antianoxic and has been known to increase the hypoxic survival of rats. Furthermore, it appears to have therapeutic efficacy in the treatment of mental illnesses and rheumatic diseases.

A few investigations into the anti-viral properties of DMSO have been carried out. Remission of crinkle strawberry virus symptoms in *Fragaria vesca* resulted from spraying infected plants with 500 ppm DMSO containing 500 ppm of 6-mercaptopurine or 100 ppm of 6-methylpurine. Suppression of symptoms and a change in the syndromes of peach mosaic (PMV) and necrotic ringspot viruses (NRSV) resulted from injection of peach trees with DMSO. However, very mild forms of the viruses were subsequently found in the trees. Local lesion symptoms of tobacco mosaic virus (TMV) in several hosts were reduced by mixing 0.05 to 1% DMSO with virus before innoculation (The Sulphur Institute Journal, Autumn 1969, 2–6).

The effect of DMSO on the infectivity of four RNA and two DNA viruses has also been studied (Chan and Gadebusch, Applied Microbiology, vol. 16, no. 10, 1625–1626, 1968). At a concentration of 80% in buffered saline DMSO inactivated the infectivity of every virus tested. However, experiments designed to study the chemotherapeutic value of DMSO showed the compound to possess no beneficial effect when administered parenterally to mice infected with influenza A (PR-8) virus or Semliki Forest virus.

The stabilisation of enveloped viruses by DMSO has been studied (Wallis and Melnick, J. Virol. vol. 2, no. 9,953–954, 1968). These studies showed that concentrations of DMSO as low as 5% effectively protected the enveloped viruses under test against the trauma of freezing, i.e. the viruses were not inactivated by freezing. There was no suggestion that DMSO could be used therapeutically to combat infections attributable to enveloped viruses.

SUMMARY OF THE INVENTION

It has now been discovered that DMSO and close analogues are effective in treating infections attributable to a retrovirus. Accordingly the present invention provides a method of treating an infection attributable to a retrovirus in a human or animal patient, which method comprises the step of administering to the patient an effective amount of a compound of formula (I):

$$(R)_2S(O)_n \qquad (I)$$

wherein R is methyl or ethyl and n is 1 or 2.

The invention also provides a method of ameliorating or improving the condition of a patient suffering from an infection attributable to a retrovirus or, more particularly, to AIDS or AIDS-related complex, which method comprises the step of administering to the patient an effective amount of a compound of formula (I):

$$(R)_2S(O)_n \qquad (I)$$

wherein R is methyl or ethyl and n is 1 or 2.

DETAILED DESCRIPTION OF THE INVENTION

The present invention is concerned with the use of a compound of formula (I):

$$(R)_2S(O)_n \qquad (I)$$

wherein R is methyl or ethyl and n is 1 or 2, to treat infections attributable to a retrovirus. Preferably, the compound of formula (I) is DMSO. The retrovirus against which the compound of formula (I) may be used may be HTLV-1, HTLV-2 or a Lentivirus such as HIV-1, HIV-2, SIV or medi-visna.

The compound of formula (I) is typically formulated as a pharmaceutical composition further comprising a pharmaceutically acceptable carrier or diluent. Preferred diluents are physiologically acceptable solvents such as sterile water (Water for Injections) and physiological saline. The compounds in which n is 2 are solid at room temperature. They may therefore be initially formulated in solid form with a carrier and then dissolved in a diluent immediately prior to use. Compositions may comprise from 0.5 to 100%, for example up to 95%, of a compound of formula (I). Typical solutions for transfusion comprise from 2% to 20%, preferably from 1 to 5% such as from 1 to 3%, of a compound of formula (I). Typical solutions for intravenous injection comprise from 40 to 100% of a compound of formula (I). Pure compound of formula (I) can be used. Alternatively, solutions comprising from 50 to 80% of the compound of formula (I) may be employed. Percentages are by volume when n is 1 or by weight when n is 2.

The compounds of formula (I) are useful in combating an infection attributable to a retrovirus in humans or animals, especially in humans. They may be used to ameliorate or improve the condition of a patient. They may in particular be used to treat AIDS or AIDS-related complex (ARC).

They may be administered to a HIV-seropositive patient before development of AIDS or ARCX. The compounds are generally administered parenterally by transfusion or injection, for example intravenously, or orally. A therapeutically effective amount is given. The amount of compound administered will depend upon a variety of factors including the patient under treatment and the severity of the infection. Typically a dose of from 5 to 10 and preferably from 2.5 to 7.5 ml in the case of a compound of formula (I) in which n is 1 or g in the case of a compound of formula (I) in which n is 2 may be administered per day over a period of 5 to 10 days, once or twice per month.

The following Examples illustrate the invention. The LDV/5 cell line employed in Examples 1 and 2 is a clone of the LDV/7 cell line described in GB-A-1592954.

EXAMPLE 1

DMSO in Vitro Against HIV-1

PROCEDURE:

4 aliquots of $1 \times 10^6$ LDV/5 cells were infected with 0.5 ml of HIV-1 suspended in RPMI without serum at 37° C. (5% by volume $CO_2$) for 2 hours. Then, without removing the viral inoculum, the samples were transferred to 25 ml bottles and supplied with 6 ml of RPMI+10% by volume foetal calf serum (FCS).

IMMUNOFLUORESCENCE RESULTS:

Cells were fixed with methanol/acetone 50/50 by volume at −20° C. and processed for indirect immuofluorescence in suspension. Monoclonal antibodies M1 and M2 were used, which were directed against p17 and p24 viral proteins of HIV-1. The fluorescein isothiocyanate conjugated antibody (FITC) used was goat-antimouse with specificity for Fc fragments. The immunofluorescence positive values represent the figures after subtraction of the fluorescence background, which in no case was higher than 2.3%.

RESULTS: M1 and M2, monoclonal antibodies directed against HIV-1 p17 and p24 proteins (A) LDV/5 cells infected with HIV-1 (control)

| M1 | M2 | Days post infection |
|---|---|---|
| 6.7% | 8.2% | 14 days |
| 11.6% | 3.3% | 26 days |
| 2.4% | 5.7% | 42 days |

(B) LDV/5 cells infected with HIV-1, then transferred to medium containing 2% by volume DMSO, 3 days after infection

| M1 | M2 | Days post infection |
|---|---|---|
| 0.3% | 0% | 14 days |
| 0% | 0.3% | 26 days |
| 0.3% | 0.5% | 42 days |

(C) LDV/5 cells incubated in 2% by volume DMSO, 5 days before infection, then infected in medium without DMSO, and subsequently transferred to medium with 2% by volume DMSO

| M1 | M2 | Days post infection |
|---|---|---|
| 0.3% | 0.6% | 14 days |
| 0.8% | 0% | 26 days |

In this bottle, the cells started to die 3 days after infection. By day 24, all cells were dead (due to DMSO toxicity, not to virus-induced cell lysis).

(D) LDV/5 cells incubated in 2% by volume DMSO for 5 days before infection, then infected in absence of DMSO for two hours and, after washing, they were resuspended in normal RPMI+10% by volume FCS

| M1 | M2 | Days post infection |
|---|---|---|
| 4.2% | 2.7% | 14 DAYS |
| 3.3% | 6.1% | 26 DAYS |
| 2.0% | 5.0% | 42 days |

EXAMPLE 2

DMSO in Vitro Against SIV

LDV/5 cells were infected with SIV in the same way as for HIV-1 in Example 1. Reverse transcriptase activity was determined on day 18 and on day 25 following the infection.

RESULTS (cpm)

| | RESULTS (cpm) | | |
|---|---|---|---|
| | Control Culture | Culture 1 | Culture 2 |
| Day 18 | 68,450 | 6,506 | 54,562 |
| Day 25 | 14,380 | 4,380 | 6,456 |

Culture 1: cells were continuously incubated with 2% by volume DMSO, 3 days after viral infection.

Culture 2: cells were incubated with 2% by volume DMSO, 5 days before infection, but only until the day of infection. DMSO was then removed, and the cells were cultured in normal medium.

EXAMPLE 3

Treatment of a Patient Infected with HIV-1

This Example relates to the treatment of a male homosexual suffering from AIDS, JFL, aged 36 years. He was diagnosed serum HIV-1 positive and presented asthenia, weight loss, pulmonary tuberculosis and pneumocystosis.

The patient apparently stabilised for four months under correctional treatment, at which time a Kaposi syndrome appeared, this being treated with interferon. The general condition deteriorated: anorexia - loss in weight of nine kilos - but neither fever, nor swollen lymph glands, nor adenopathy nor intestinal problems. However, the haemogram showed very substantial anaemia, 2.5M red cells and haemoglobin level at 7.5%, ESR 93.127; leucocytes: 2,400 white (34% lymphocytes), platelets 200,000.

There was buccal and digestive candidiasis, as well as a digestive staphylococcal infection treated with injectable delayed-release Extencilline every 15 days. Then neurological disorders appeared with temporospatial disorientation and complete anterograde amnesia. Eventually, delirium appeared with hallucinations, flight of ideas and discordance. This picture was completed with speech disorders, and a neuromuscular atony rendering the patient bed-ridden.

At that time an injection of 5 ml of DMSO in 250 ml of isotonic saline was administered (2 ml/minute). This injection did not cause the appearance of any further sign. Only the characteristic odour appeared, lasting 24 hours.

48 hours later, the patient emerged from the coma, and on the next day the consciousness level returned to normal, enabling the patient to get up.

It was then observed that the patient had complete amnesia for the last twenty days until consciousness returned to normal. Memory, vigilance and the field of consciousness remained normal and stable. On that day, the patient returned home and received a second injection of DMSO under the same conditions as the first. Only a febricula of 38° C. persisted, in the evening, and a dry irritation cough. The clincal improvement lasted for 15 days.

EXAMPLE 4

DMSO in Vitro Against HIV-1

The effect of DMSO on HIV-1 infection of LDV/7 cells was studied. 4 aliquots of $1 \times 10^6$ LDV/7 cells were infected with 0.5 ml of HIV-1 suspended in RPMI without serum at 37° C. (5% by volume $CO_2$) for 2 hours. Then, without removing the viral inoculum, the samples were transferred to 25 ml bottles and supplied with 6 ml of RPMI+10% by volume FCS. Enzyme-linked immunosorbent assay (ELISA) for the HIV-1 p24 antigen was then effected on the cell culture supernatants using a NEN (Trade Mark) kit Du Pont).

RESULTS

The results are shown below. The values in the second to sixth columns are amounts of p24, expressed as ng/ml.

| DAYS POST INFECTION | EXPERIMENT | | | | |
|---|---|---|---|---|---|
| | A | B | C | D | E |
| 7 | 0.24 | 0.06 | 0.13 | 0.02 | 0.19 |
| 13 | 0.016 | 0.02 | 0.07 | 0.10 | 0.07 |
| 20 | 1.70 | 0.05 | 0.03 | 0.08 | 0.07 |
| 33 | 0.08 | 0.12 | 0.02 | 1.45 | 0.95 |

A:HIV-1 infection control
B:Cells kept in medium and 2% DMSO after infection
C:Cells preincubated in 2% DMSO for 5 days before infection, then kept in medium and 2% DMSO after infection
D:Cells preincubated in 2% DMSO for 5 days before infection, then kept in medium without DMSO after infection.
E:Samples from cell cultures, infected with HIV-1 preincubated for 24 hours in 2% DMSO. The cells were kept in medium without DMSO before and after infection.

I claim:

1. A method of treating an infection attributable to a retrovirus in a human or animal patient suffering from such infection, which method comprises the step of administering to said patient an effective amount to control said infection, of a compound of formula (I):

$$(R)_2S(O)_n \qquad (I)$$

wherein R is methyl or ethyl and n is 1 or 2.

2. A method according to claim 1, wherein the compound of formula (I) is dimethylsulphoxide.

3. A method according to claim 1, wherein the said infection is attributable to HTLV-1, HTLV-2 or a Lentivirus.

4. A method according to claim 3, wherein the Lentivirus is HIV-1, HIV-2, SIV or medi-visna.

5. A method according to claim 1, wherein the compound of formula (I) is used to treat a patient with AIDS or AIDS-related complex.

6. A method according to claim 1 wherein the compound of formula (I) is used to treat a patient who is HIV-seropositive but who has not developed AIDS or AIDS-related complex.

7. A method according to claim 1, wherein a 1 to 5% solution of the compound of formula (I) in which the percentage is by volume when n is 1 and by weight when n is 2 in formula (I) is administered to a patient by transfusion.

8. A method according to claim 1, wherein a 50 to 80% solution of the compound of formula (I) in which the percentage is by volume when n is 1 and by weight when n is 2 in formula (I) is administered to a patient by intravenous injection.

9. A method of ameliorating or improving the condition of a patient suffering from an infection attributable to a retrovirus which method comprises the step of administering to the patient an effective amount to ameliorate or improve the condition of said patient, of a compound of formula (I):

$$(R)_2S(O)_n \qquad (I)$$

wherein R is methyl or ethyl and n is 1 or 2.

10. A method of ameliorating or improving the condition of a patient suffering from AIDS or AIDS-related complex or who is HIV-seropositive but who has not developed AIDS or AIDS-related complex, which method comprises the step of administering to the patient an effective amount to ameliorate or improve the condition of said patient of a compound of formula (I):

$$(R)_2S(O)_n \qquad (I)$$

wherein R is methyl or ethyl and n is 1 or 2.

* * * * *